United States Patent [19]

Welter et al.

[11] 4,454,068

[45] Jun. 12, 1984

[54] CYCLOALKYL DERIVATIVES OF BENZISOSELENAZOLONES

[75] Inventors: André Welter,

[73] Assignee: A. Nattermann & Cie GmbH, Cologne, Fed. Rep. of Germany

[21] Appl. No.: 513,088

[22] Filed: Jul. 12, 1983

[30] Foreign Application Priority Data

Jul. 14, 1982 [DE] Fed. Rep. of Germany ....... 3226286

[51] Int. Cl.³ .................... C07D 293/12; A61K 31/33
[52] U.S. Cl. ................................. 260/239 R; 424/244
[58] Field of Search ..................................... 260/239 R

[56]     References Cited
       FOREIGN PATENT DOCUMENTS 44971  2/1982  European Pat. Off. ........ 260/239 R

OTHER PUBLICATIONS

Chemical Abstract vol. 92, 1980, Weber et al, p. 638 92:110771j.

*Primary Examiner*—Mary C. Lee
*Assistant Examiner*—Cecilia Shen
*Attorney, Agent, or Firm*—Pearne, Gordon, Sessions, McCoy, Granger & Tilberry

[57]            ABSTRACT

The invention relates to new benzisoselenazolones of the general formula I

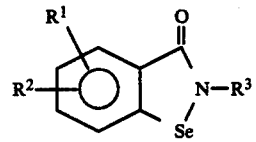

and to the use thereof in the treatment of inflammatory diseases in humans.

8 Claims, No Drawings

CYCLOALKYL DERIVATIVES OF BENZISOSELENAZOLONES

The present invention relates to new benzisoselenazolones and to their use as active ingredients in the treatment of inflammatory diseases of the rheumatic type.

The compounds according to the invention correspond to the general formula I

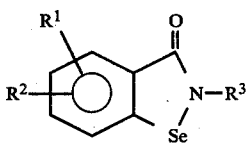

in which $R^1$ and $R^2$ can be identical or different and, independently of one another, denote hydrogen, halogen, $C_1$-$C_4$-alkyl, $C_1$-$C_4$-alkoxy, hydroxyl, trifluoromethyl, nitro, di-($C_1$-$C_4$-alkyl)-amino, or $R^1$ and $R^2$ together denote methylenedioxy, while $R^3$ denotes a cycloalkyl radical having 5 to 10 carbon atoms which optionally has a double bond.

In this context, compounds in which $R^1$ and $R^2$ can be identical or different and, independently of one another, denote hydrogen, fluorine, chlorine, bromine, hydroxyl, methoxy, methyl, trifluoromethyl, nitro and/or methylenedioxy, while $R^3$ denotes a cyclopentyl, cyclopentenyl, cyclohexyl, cyclohexenyl, cycloheptyl, cycloheptenyl, cyclooctyl, cyclooctenyl, norbornyl, hexahydroindanyl, hexahydronaphthyl or adamantyl radical, are preferred.

Compounds in which $R^1$ and $R^2$ can be identical or different, and, independently of one another, denote hydrogen, chlorine, methyl, methoxy, nitro and/or methylenedioxy, while $R^3$ denotes a cyclohexyl, 2-cyclohexenyl or 3-cyclohexenyl radical, are particularly preferred.

Examples of the compounds according to the invention are as follows:
2-cyclopentyl-1,2-benzisoselenazol-3(2H)-one,
2-(3-cyclopenten-1-yl)-1,2-benzisoselenazol-3(2H)-one,
2-cyclohexyl-1,2-benzisoselenazol-3-(2H)-one,
6-methyl-2-cyclohexyl-1,2-benzisoselenazol-3(2H)-one,
6-methoxy-2-cyclohexyl-1,2-benzisoselenazol-3(2H)-one,
6-chloro-2-cyclohexyl-1,2-benzisoselenazol-3(2H)-one,
5-nitro-2-cyclohexyl-1,2-benzisoselenazol-3(2H)-one,
5-chloro-2-cyclohexyl-1,2-benzisoselenazol-3(2H)-one,
7-methoxy-2-cyclohexyl-1,2-benzisoselenazol-3(2H)-one,
5,6-methylenedioxy-2-cyclohexyl-1,2-benzisoselenazol-3(2H)-one,
2-(2-cyclohexen-1-yl)-1,2-benzisoselenazol-3(2H)-one,
2-(3-cyclohexen-1-yl)-1,2-benzisoselenazol-3(2H)-one,
2-cycloheptyl-1,2-benzisoselenazol-3(2H)-one,
2-(3-cyclopenten-1-yl)-1,2-benzisoselenazol-3(2H)-one,
2-cyclooctyl-1,2-benzisoselenazol-3(2H)-one,
2-(4-cyclocten-1-yl)-1,2-benzisoselenazol-3(2H)-one,
2-(2-norbornyl)-1,2-benzisoselenazol-3(2H)-one,
2-(2-hexahydroindanyl)-1,2-benzisoselenazol-3(2H)-one,
2-(3-hexahydroindanyl)-1,2-benzisoselenazol-3(2H)-one,
2-(1-hexahydronaphthyl-1,2-benzisoselenazol-3(2H)-one,
2-(2-hexahydronaphthyl)-1,2-benzisoselenazol-3(2H)-one,
2-(1-adamantyl)-1,2-benzisoselenazol-3(2H)-one, and
2-(2-adamantyl)-1,2-benzisoselenazol-3(2H)-one.

The benzisoselenazolones of the formula I according to the invention can be used for the treatment of a large number of diseases, such as, for example, for the prophylaxis and therapy of infectious diseases, for stimulating the immune system or for selenium deficiency diseases, as defined by W. Kraus and P. Oehme, Das Deut. Gesundheitswesen, 1979, 34 (37), 1713–1718 and 1979, 34 (37), 1769–1773.

However, the benzisoselenazolones of the formula I are particularly distinguished by antiarteriosclerotic and antiinflammatory properties. They are particularly suitable for the therapy of rheumatic diseases, such as, for example, arthroses or chronic infective arthritis, the new compounds being distinguished by being very well tolerated because they are non-toxic and, in contrast to known antiinflammatory therapeutic agents, exhibit no ulcer formation or gastrointestinal irritation.

The new benzisoselenazolones of the general formula I can be obtained in a manner known per se. In this, an o-chloroselenobenzoyl chloride of the formula II

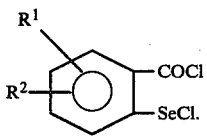

$R^1$ and $R^2$ having the meaning indicated in formula I, is reacted with a cycloalkylamine of the formula III $R^3$—$NH_2$          III $R^3$ having the meaning indicated in formula I, under conditions of ring closure to give benzisoselenazolones of the formula I.

The preparation of the appropriate o-chloroselenobenzoyl chlorides is carried out by the process of A. Ruwet and M. Renson, Bull. Soc. Chim. Belg. 1966, 15, 157–163.

Examples of suitable starting compounds of the formula II are the following compounds:
2-chloroselenobenzoyl chloride,
2-chloroseleno-4-chlorobenzoyl chloride,
2-chloroseleno-4-methylbenzoyl chloride,
2-chloroseleno-4-methoxybenzoyl chloride,
2-chloroseleno-5-chlorobenzoyl chloride,
2-chloroseleno-5-methoxybenzoyl chloride,
2-chloroseleno-5-nitrobenzoyl chloride,
2-chloroseleno-3-methoxybenzoyl chloride, and
2-chloroseleno-3,4-methylenedioxybenzoyl chloride.

Examples of suitable starting compounds III are the following:
cyclopentylamine, 4-amino-1-cyclopentene,
cyclohexylamine, 3-amino-1-cyclohexene,
4-amino-1-cyclohexene, cycloheptylamine,
5-amino-1-cycloheptene, cyclooctylamine,
5-amino-1-cycloocten, 2-norbornylamine,
2

The present invention also relates to pharmaceutical products containing compounds of the formula I. The pharmaceutical products according to the invention are those for enteral, such as oral or rectal, and parenteral administration which contain the pharmaceutical active ingredients alone or together with a customary vehicle which can be used pharmaceutically. The pharmaceutical formulation of the active ingredient is advantageously in the form of single doses adjusted to be appropriate for the desired administration, such as, for example, tablets, coated tablets, capsules, suppositories, granules, solutions, emulsions or suspensions. The dosage of the compounds is customarily between 10 and 1,000 mg per day, preferably between 30 and 300 mg, and this can be administered once or several times, preferably two to three times a day.

The preparation of the compounds according to the invention is illustrated in more detail by the following examples.

EXAMPLE 1

2-cyclohexyl-1,2-benzisoselenazol-3(2H)-one 4.7 g (0.074 mol) of cyclohexylamine, dissolved in 80 ml of carbon tetrachloride, are slowly added dropwise, with stirring and cooling in ice (temperature < 10° C.) under a nitrogen atmosphere, to a solution of 4 g (0.015 mol) of o-chloroselenobenzoyl chloride in 60 ml of carbon tetrachloride. After stirring at room temperature for 1 hour, the precipitate which has separated out is filtered off, washed with a little carbon tetrachloride, 0.5-normal hydrochloric acid and water, dried and recrystallised from carbon tetrachloride and then toluene.

Yield: 3.1 g (70% of theory), melting point 159°–160° C.

IR (in KBr): 1590 cm$^{-1}$

MS [m/e]: 281 (24.8%), 199 (100%), 184 (16.5%), 156 (14.2%).

The following are prepared in analogy to the procedure in Example 1:

EXAMPLE 2

2-(2-cyclohexen-1-yl)-1,2-benzisoselenazol-3(2H)-one.

Yield: 67% of theory, melting point 142°–143° C.

IR (in KBr): 1585 cm$^{-1}$

MS [m/e]: 279 (42.3%), 199 100%), 184 (45.2%), 156 (11.6%), 80 (96.9%).

EXAMPLE 3

2-(3-cyclohexen-1-yl)-1,2-benzisoselenazol-3(2H)-one.

Yield: 66% of theory, melting point 169°–171° C.

IR (in KBr): 1610 cm$^{-1}$

MS [m/e]: 279 (17.5%), 225 (19.7%), 200 (100%), 184 (18.6%), 156 (27.3%), 80 (76.0%).

The following are prepared in analogy to the procedure in Example 1:
2-cyclopentyl-1,2-benzisoselenazol-3(2H)-one,
6-methyl-2-cyclohexyl-1,2-benzisoselenazol-3(2H)-one,
6-methoxy-2-cyclohexyl-1,2-benzisoselenazol-3(2H)-one,
6-chloro-2-cyclohexyl-1,2-benzisoselenazol-3(2H)-one,
5-nitro-2-cyclohexyl-1,2-benzisoselenazol-3(2H)-one,
5-chloro-2-cyclohexyl-1,2-benzisoselenazol-3(2H)-one,
7-methoxy-2-cyclohexyl-1,2-benzisoselenazol-3(2H)-one,
5,6-methylenedioxy-2-cyclohexyl-1,2-benzisoselenazol-3(2H)-one,
2-cycloheptyl-1,2-benzisoselenazol-3(2H)-one,
2-(3-cyclopenten-1-yl)-1,2-benzisoselenazol-3(2H)-one,
2-cyclooctyl-1,2-benzisoselenazol-3(2H)-one,
2-(4-cycloocten-1-yl)-1,2-benzisoselenazol-3(2H)-one,
2-(2-norbornyl)-1,2-benzisoselenazol-3(2H)-one,
2-(2-hexahydroindanyl)-1,2-benzisoselenazol-3(2H)-one,
2-(3-hexahydroindanyl)-1,2-benzisoselenazol-3(2H)-one,
2-(1-hexahydronaphthyl)-1,2-benzisoselenazol-3(2H)-one,
2-(2-hexahydronaphthyl)-1,2-benzisoselenazol-3(2H)-one,
2-(1-adamantyl)-1,2-benzisoselenazol-3(2H)-one, and
2-(2-adamantyl)-1,2-benzisoselenazol-3(2H)-one.

What we claim is:

1. Benzisoselenazolones of the general formula I

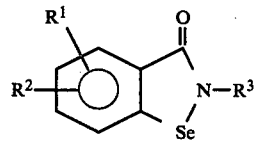

wherein R$^1$ and R$^2$ which are the same or different from each other, represent members selected from the group consisting of hydrogen, halogen, C$_1$–C$_4$-alkyl, C$_1$–C$_4$-alkoxy, hydroxyl, trifluoromethyl, nitro, di-(C$_1$–C$_4$-alkyl)-amino, and, R$^1$ and R$^2$ together, methylenedioxy, and R$^3$ is a member selected from the group consisting of the cycloalkyl groups having from 5 to 10 carbon atoms and the cycloalkenyl groups having from 5 to 10 carbon atoms and having a double bond.

2. Benzisoselenazolones according to claim 1 wherein R$^1$ and R$^2$, which are the same or different from each other, represent members selected from the group consisting of hydrogen, fluorine, chlorine, bromine, hydroxyl, methoxy, methyl, trifluoromethyl, nitro and, R$^1$ and R$^2$ together, methylenedioxy, and R$^3$ is a member selected from the group consisting of cyclopentyl, cyclopentenyl, cyclohexyl, cyclohexenyl, cycloheptyl, cycloheptenyl, cyclooctyl, cyclooctenyl, norbornyl, hexahydroindanyl, hexahydronaphthyl and adamantyl.

3. Benzisoselenazolones according to claim 1 wherein R$^1$ and R$^2$, which are the same or different from each other, represent a member selected from the group consisting of hydrogen, chlorine, methyl, methoxy, nitro and, R$^1$ and R$^2$ together, methylenedioxy, and R$^3$ is a member selected from the group consisting of cyclohexyl, 2-cyclohexenyl and 3-cyclohexenyl.

4. 2-Cyclohexyl-1,2-benzisoselenazol-3(2H)-one.

5. 6-Chloro-2-cyclohexyl-1,2-benzisoselenazol-3(2H)-one.

6. 6-Methoxy-2-cyclohexyl-1,2-benzisoselenazol-3(2H)-one.

7. 2-(2-Cyclohexen-1-yl)-1,2-benzisoselenazol-3(2H)-one.

8. 2-(3-Cyclohexen-1-yl)-1,2-benzisoselenazol-3(2H)-one.

* * * * *

UNITED STATES PATENT AND TRADEMARK OFFICE
CERTIFICATE OF CORRECTION

PATENT NO. : 4,454,068
DATED : June 12, 1984
INVENTOR(S) : Andre Welter et al.

It is certified that error appears in the above—identified patent and that said Letters Patent is hereby corrected as shown below:

Section [75] on the face of the patent should be amended as follows:

--Inventors:  Andre Welter, Pulheim, Fed. Rep. of Germany;
              Sigurd Leyck, Pulheim, Fed. Rep. of Germany; and
              Eugen Etschenberg, Cologne, Fed. Rep. of Germany --.

Column 2, line 63, after "2" the following should be inserted:

--    -aminohexahydroindane, 3-aminohexahydroindane,
      1-naphthylamine, 2-naphthylamine,
      1-adamantylamine and 2-adamantylamine. --

Signed and Sealed this

Twelfth Day of February 1985

[SEAL]

Attest:

DONALD J. QUIGG

Attesting Officer    Acting Commissioner of Patents and Trademarks